US008556872B1

(12) United States Patent
Hamman et al.

(10) Patent No.: US 8,556,872 B1

(45) Date of Patent: Oct. 15, 2013

(54) NOISE ATTENUATING HIGH-VOLUME SUCTION TIP WITH AUTOMATIC INTEGRAL ON DEMAND VACUUM RELEASE VALVE MECHANISM

(71) Applicants: James E. Hamman, Washburn, WI (US); James B. Vee, Iron River, WI (US); Frances K. Hamman, Alexandria, VA (US)

(72) Inventors: James E. Hamman, Washburn, WI (US); James B. Vee, Iron River, WI (US); Frances K. Hamman, Alexandria, VA (US)

( * ) Notice: Subject to any disclaimer, the term of this patent is extended or adjusted under 35 U.S.C. 154(b) by 0 days.

(21) Appl. No.: 13/674,785

(22) Filed: Nov. 12, 2012

(51) Int. Cl.
*A61B 19/00* (2006.01)

(52) U.S. Cl.
USPC .......................................... 604/319; 604/317

(58) Field of Classification Search
None
See application file for complete search history.

(56) References Cited

U.S. PATENT DOCUMENTS 4,204,328 A 5/1980 Kutner
5,509,802 A 4/1996 Whitehouse et al.
2011/0040285 A1* 2/2011 Boyle .......................... 604/540

OTHER PUBLICATIONS

Practicon—Practical for Dentisty, "WhisperSafe™ HVE Tips" and additional view, http://practicon.com/WhisperSafe%E2%84%A2-HVE-Tips/p/71-19710/, retrieved on Nov. 27, 2012, 3 pp.

* cited by examiner

*Primary Examiner* — Leslie Deak
*Assistant Examiner* — Sara Sass
(74) *Attorney, Agent, or Firm* — Shumaker & Seiffert, P.A.

(57) ABSTRACT

In one embodiment, the present disclosure is directed to a high volume suction tip, including a tubular body with peripheral side wall, a functional orifice, and a vacuum source end. An aperture in a wall of the tubular body forms a vacuum release orifice, wherein the aperture is between the functional orifice and the vacuum source end. A plurality of tubes are placed within a lumen of the tubular body, wherein the tubes have a longitudinal axis substantially parallel to a longitudinal axis of the tubular body and provide at least one channel for transmitting a material from the functional orifice to the vacuum source end. A first tube occludes the vacuum release orifice at a first pressure, and, at a second pressure lower than the first pressure, a compressible side wall of a second tube collapses inwardly to disengage the first tube from the vacuum release orifice.

19 Claims, 5 Drawing Sheets

NOISE ATTENUATING HIGH-VOLUME SUCTION TIP WITH AUTOMATIC INTEGRAL ON DEMAND VACUUM RELEASE VALVE MECHANISM

BACKGROUND

High volume suction is often used in medical and dental surgical procedures. Maintenance of a clear operating field necessitates removal of any fluids, solids or materials that would inhibit clear visualization of the surgical field. This vacuum evacuation maintains patient safety by preventing aspiration of fluid or other materials generated or liberated from surgical procedure such as blood, saliva, irrigation fluids, chemicals, as well as aerosolized vaporized debris from tissues from high speed drilling, laser cutting, electrocautery, or other modalities needed for completion of surgical procedures.

Due to the intensity of the vacuum and high flow characteristics of most suction tip designs, the suction tip has a fixed vacuum release orifice to prevent iatrogenic vacuum tissue impingement and damage, or retrograde back flow of materials, by maintenance of a opening in direct fluid intimate contact with the surgical field and the interior of the suction tip to equalize pressure if the main orifice is occluded. The vacuum release orifice, if present, is open at all times. If the tip lacks this orifice, vacuum of delicate tissues could result in damage to the patient as well as possibly contributing to cross contamination by back flow. Thus the vacuum release orifice is a beneficial and useful design aspect of the high volume suction tip.

SUMMARY

In one embodiment, the present disclosure is directed to a high volume suction tip, including a tubular body with peripheral side wall, a functional orifice, and a vacuum source end. An aperture in a wall of the tubular body forms a vacuum release orifice, wherein the aperture is between the functional orifice and the vacuum source end. A plurality of tubes are placed within a lumen of the tubular body, wherein the tubes have a longitudinal axis substantially parallel to a longitudinal axis of the tubular body and provide at least one channel for transmitting a material from the functional orifice to the vacuum source end. A first tube occludes the vacuum release orifice at a first pressure. At a second pressure lower than the first pressure, a compressible side wall of a second tube collapses inwardly to disengage the first tube from the vacuum release orifice.

In another embodiment, this disclosure is directed to a system including a vacuum source; a suction conduit attached to the vacuum source, and a suction tip on the suction conduit. The suction tip includes a tubular body with peripheral side wall, a vacuum source end attached to the suction conduit, and a functional orifice distal the vacuum source end. A vacuum release orifice including an aperture in a wall of the tubular body is between the functional orifice and the vacuum source end. A plurality of tubes reside within a lumen of the tubular body, wherein the tubes have a longitudinal axis substantially parallel to a longitudinal axis of the tubular body and provide at least one channel for transmitting a material from the functional orifice to the vacuum source end. A first tube occludes the vacuum release orifice at a first pressure, and wherein at a second pressure lower than the first pressure, a compressible side wall of a second tube collapses inwardly to disengage the first tube from the vacuum release orifice.

In yet another embodiment, the present disclosure is directed to a kit including a suction conduit; a suction tip including a tubular body with peripheral side wall, a vacuum source end suitable for attachment to the suction conduit, and a functional orifice distal the vacuum source end, and a vacuum release orifice including an aperture in a wall of the tubular body between the functional orifice and the vacuum source end. The kit further includes at least one compressible tube suitable for insertion into a lumen of the tubular body, wherein, when inserted into the lumen, a surface of the at least one tube occludes the vacuum release orifice.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the drawings indicate like elements.

DETAILED DESCRIPTION

Figure 1A:
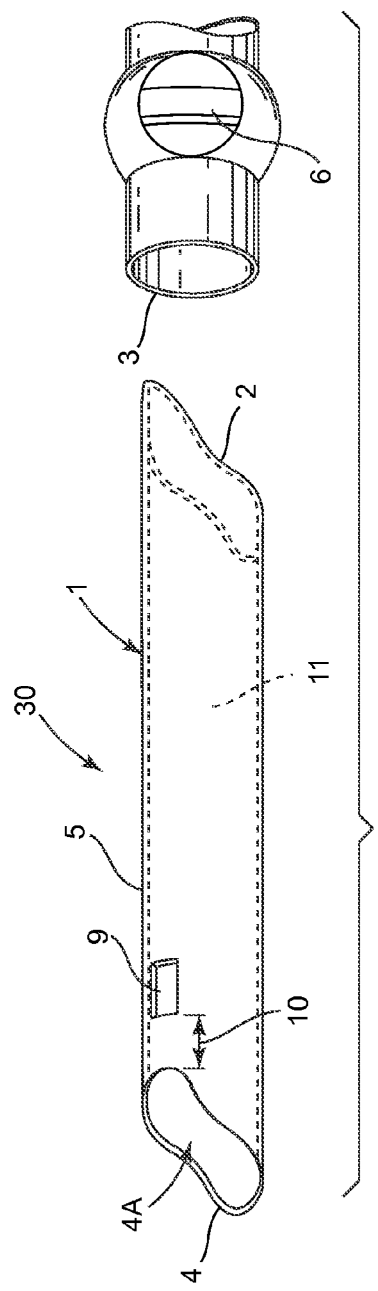
FIG. 1A is a schematic plan view of a conventional suction tip apparatus with a singular open lumen and a vacuum release orifice.

During vacuum operations, particularly in medical and dental surgical procedures, flow of gases, liquids and materials through the lumen of a suction tip produces a high level of noise. Since the functional orifice of the suction tip is open at all times, the high velocity gas passage produces a characteristic high frequency whistle or noise of high db level that can be disagreeable to the patient and operators. This high frequency whistling sound also has negative long term effects to the sense of hearing of those using such devices due to chronic exposure to high decibel level noise that is sustained and repetitive and continues while the vacuum is being used. This type of hearing loss and frequency damage has been observed and documented following chronic exposure to the high speed dental air turbine.

High volume suction tip flow characteristics also are less laminar, thus noisy, due to the vacuum release orifice producing turbulence within the lumen of the suction tip itself. Also, due to a completely open lumen of most high volume suction tips, not only is flow is intrinsically more turbulent, but inadvertent evacuation of items needed in the surgical field can occur, such as sponges, cotton items, precious metal or ceramic restorations used in dentistry, surgical implements and other small objects that would otherwise not be desired to be lost or retrieved from a biohazard waste trap downstream from the surgical field.

The present disclosure is directed to a noise attenuating high volume suction tip with an integral automatic on demand vacuum release valve mechanism. In one preferred embodiment, this device is intended to be connected to a vacuum system producing high volume negative pressure flow to remove desired materials from the oral environment or surgical field without excessive noise or potential for iatrogenic tissue impingement and damage, fluid back flow and inadvertent evacuation of debris that could block vacuum flow downstream from the surgical field. However, the suction tip can be used in any application utilizing vacuum suction, and is not limited to medical or dental surgical procedures.

A plurality of internal parallel tubes within a lumen of a larger-diameter main body of the suction tube produces more laminar flow within the tube, which attenuates noise. At least one of these multiple internal parallel tubes within the main body are thin walled, resilient and compressible, which creates frictional or fixed intimate contact between the internal surfaces of the main body and the exterior surfaces of the tubes.

The elastic and resilient internal tubes create a physical barrier to prevent evacuation of items larger than the diameter of the internal tubes such that inadvertent removal of items from surgical field that could clog the vacuum system in a non retrievable way is eliminated by not allowing any large materials to be suctioned and lost. The items would be caught within the orifice of the suction tube.

The internal tubes also press against the internal surface of the main body of the suction tip and a sidewall of a first tube seals and occludes the vacuum release orifice under normal vacuum function, which eliminates turbulence and whistle. If the functional end of the suction tip becomes occluded, a side wall of a second tube collapses inwardly under the higher external pressure differential with respect to the vacuum source and maintains airflow through the main tube body of the high volume suction tip. This inward movement of the second tube causes the sidewall of the first tube to move away from and uncover the vacuum release orifice. This system ensures the vacuum release orifice is functionally automatically open on demand only when needed, and otherwise remains closed to minimize noise produced by turbulent flow around the vacuum release orifice. Thus, the internal tubes provide a two-fold functionality of noise reduction by laminar flow as well as elimination of turbulence of the vacuum release orifice.

Figure 1B:
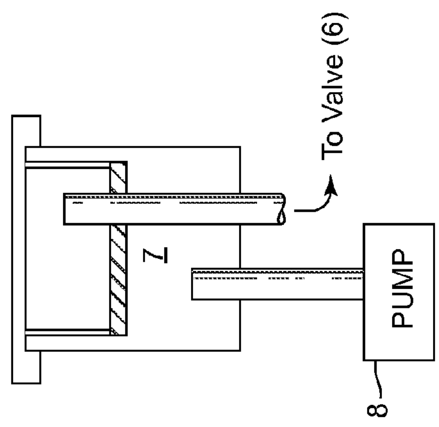
FIG. 1B is a schematic diagram of a downstream vacuum trap used with the suction tip apparatus of FIG. 1A.

Referring to FIGS. 1 and 2, a high volume suction tip 30 includes a tubular body 1. The tubular body 1 has two ends: a vacuum source end 2, which is attached to a vacuum source 3, and a functional orifice 4A used in suctioning operations such as, for example, to evacuate materials from a surgical field. The tubular body 1 has a peripheral side wall 5 that encloses the vacuum passage(s) 11 within the lumen of the tubular body 1. The vacuum passage 11 is the primary path for all gases, fluid and materials evacuated through the tubular body 1 between the functional orifice 4A and the vacuum source end 2 and into the vacuum source 3, past vacuum on-off valve 6, ultimately into a downstream vacuum trap 7 and a vacuum apparatus 8 (FIG. 1B).

The peripheral side wall 5 also includes an aperture that forms a vacuum release orifice 9. The vacuum release orifice 9 provides secondary vacuum pathway if the functional orifice 4A is occluded. The vacuum release orifice 9 is spaced from the functional orifice 4A by a distance 10 which is usually less than one half the distance between the vacuum source end 2 and the functional tip 4 towards either the functional orifice 4A, or the vacuum source end 2. The vacuum release orifice 9 extends through and is formed by the sidewall 5 in direct fluid intimate contact with the vacuum passage 11, providing a secondary orifice for vacuum flow to the primary functional orifice 4. In the conventional device shown in FIG. 1A, the vacuum release orifice 9 is designed to remain open at all times.

Figure 2A:
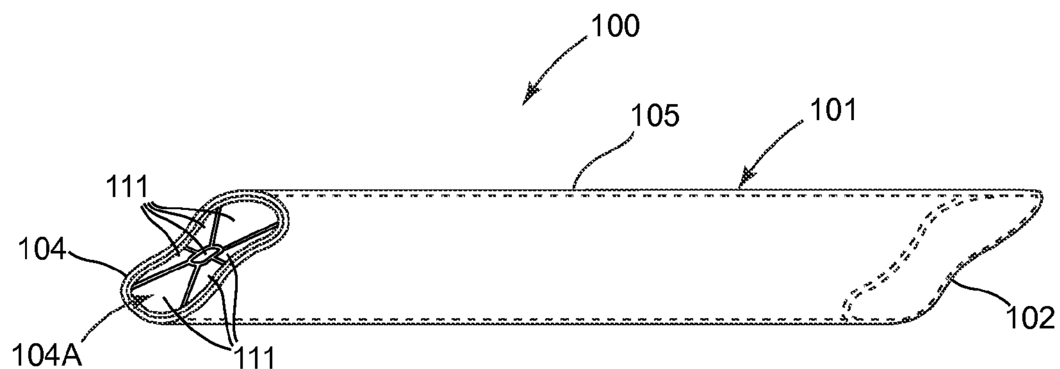
FIG. 2A is a plan view of a conventional suction tip apparatus with thick walled extrusion and no vacuum release orifice.
Figure 2B:
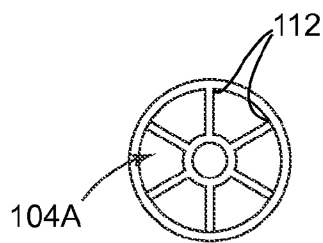
FIG. 2B is a cross-sectional view of the suction tip apparatus shown in FIG. 2A.

FIG. 2A refers to another embodiment of a high volume evacuator tip 100, which includes all the components of FIG. 1A, except the vacuum release orifice 9. Absence of a vacuum release orifice can permit back flow of contaminated material through 101 between the functional tip 104 and the vacuum source end 102 if the end 102 is occluded, thus allowing for vacuum pressure build up and spontaneous release of a pressure differential. A second negative characteristic of the device shown in FIG. 2A is the combined surface area of the peripheral wall creating vacuum passage(s) 111, which results in reduction of volumetric flow. The decreased volumetric flow results from functionally decreasing the volume of the functional orifice 104A and volume of the vacuum passage 111, as well as by the creation of sharp internal line angles 112 created by the peripheral side wall 105 as noted in FIG. 2B. The sharp internal line angle 112 of the vacuum passage 111 results in non-laminar flow through the vacuum passage 111.

Figure 3A:
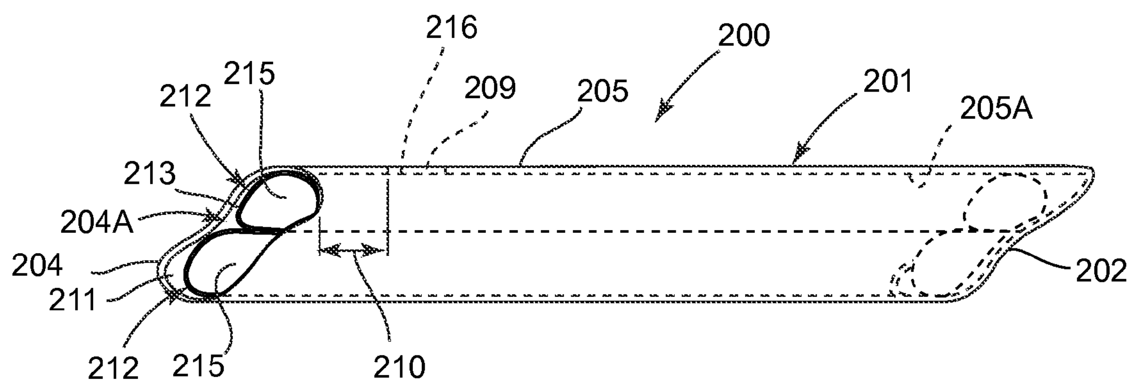
FIG. 3A is a plan view of an embodiment of a noise-attenuating high volume suction tip apparatus with integral automatic vacuum release valve mechanism.

FIG. 3A shows a suction tip 200 that includes a tubular body 201 with a vacuum source end 202 attached to a vacuum source (not shown in FIG. 3A, see FIG. 1A), and a functional orifice 204A used to evacuate materials from surgical field. The tubular body 201 has a peripheral side wall 205 with an interior surface 205A. The peripheral side wall 205 also includes a vacuum release orifice 2 0 9, which provides a secondary vacuum pathway if the functional orifice 204A is occluded. The vacuum release orifice 209 is spaced from the functional orifice 204A by a distance 210 which is usually less than one half the distance between the vacuum source end 202 and the functional tip 204 towards either the functional orifice 204A, or the vacuum source end 202. The vacuum release orifice 209 extends through and is formed within the sidewall 205. When open, the vacuum release orifice 209 provides a secondary opening for vacuum flow to the primary functional orifice 204A.

Referring to FIG. 39, the vacuum release orifice 209 is designed to remain closed unless needed. The present disclosure is directed to an on-demand valving mechanism 216 for the vacuum release orifice 209. This on-demand valving mechanism 216 is created by the insertion of at least one compressible tubular structure within the lumen of the main tubular body 201.

Figure 3B:
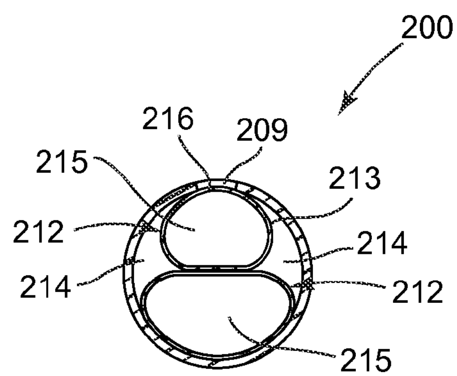
FIG. 3B is a cross-sectional view of the suction tip apparatus of FIG. 3A.
Figure 4:
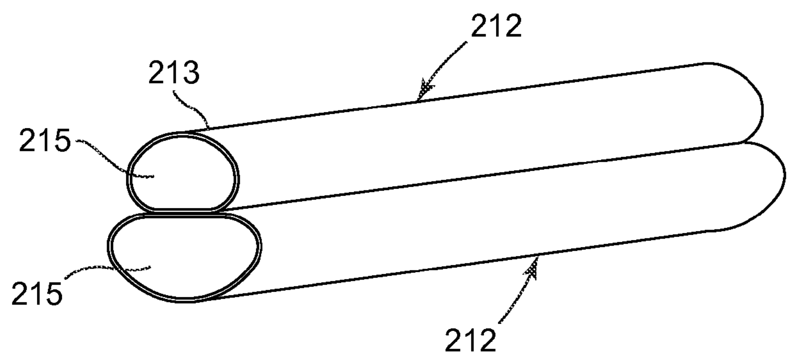
FIG. 4 is a schematic plan view of an embodiment of a tubular insert suitable for use of the suction tip apparatus of FIG. 3A.

In the embodiment shown in FIGS. 3A-3B and 4, enclosed within the vacuum passage of the suction tip 201 are a number of tubes 212, of which at least one has a side wall that is thin, compressible and resilient. An exterior surface 213 of a first one of the tubes is placed in contact with the interior surface 205A and seals the vacuum release orifice 209. The tubes 212 are in direct intimate contact with the interior surface 205A of the peripheral side wall 205 of the main tubular body 201, and have a longitudinal axis generally parallel to the longitudinal axis of the tubular body 201. Insertion of the thin walled resilient tubes 212 into the tubular body 201 results in a minor compression of at least one of the thin walled tubes 212, which provides a frictional fit within the lumen of the tubular body 201 and causes the first tube 212 to dose off and seal the vacuum release orifice 209.

The tubes 212 can be frictionally and/or fixably retained within the main tubular body 201 and thus removable or replaceable, fixed at the vacuum source end 202, or fixed and/or frictionally fit at the functional tip 204. The tubes 212 may be fixed to the tubular body 201 in any suitable way, including, but not limited to, ultrasonic welding, adhesives, mechanical lock, press fit or other retentive modalities as desired for manufacture. In some embodiments, the tubes 212 can be removable and disposable, or may be autoclaveable or otherwise re-useable.

In some embodiments, the tubes 212 could be packaged in a kit form and/or adapted to fit in otherwise conventional vacuum tips. In other embodiments, any of the tubes 212 and the tubular body 201 could be packaged in sterile kit form with a suitable vacuum conduit (see, e.g., conduit 3 in FIG. 1A), as well as optional operating instructions.

Suitable materials for the tubular body 201 and the tubes 212 include, for example, plastics such as high-density polyethylene (HDPE), polytetrafluoroethylene (PTFE), polypropylene, acrylic, polyvinylchloride (PVC), ultra-high molecular weight polyethylene (UHMW-PE), polypropylene (PP), polystyrene (PS) and the like, composites and carbon fibers, as well as metals such as stainless steel or titanium. The polymers and composites may be modified with suitable additives to provide the desired levels of flexibility and conformability.

The tubes 212 may have a variety of diameters, thicknesses, geometries and overall number as necessary to tune and optimize the flow characteristics through the tubular body 201 for a particular application. The ends of the tubes 212 may be placed a predetermined distance d from the functional orifice 204 (see, for example, FIG. 6B), yet still cover and seal the vacuum release orifice 209, such that the functional orifice 204 creates a space/trap region (see, for example, trap 404 in FIG. 6A) that can catch items dislodged during suctioning procedures. The plurality of tubes 212 can be staggered or placed at differing distances from the functional orifice 204 as to impart a multiplicity of trap sizes or flow characteristic as desired (see, for example, FIG. 6C).

At least one of the tubes 212 has a side wall that is thin, flexible, and resilient. An exterior surface 213 of a first tube 212 occludes and seals the vacuum release orifice 209 as the functional tip 204 is used at a normal operating pressure in suctioning procedures. This sealing of the vacuum release orifice 209 eliminates the turbulence and noise associated with the materials passing through the functional orifice 204A and past the vacuum release orifice 209. As shown in FIG. 3B, the tubes 212 form primary flow channels 215, as well as at least one peripheral accessory channel 214, between the peripheral exterior side wall 213 of the tubes 212 and the interior surface 205A of the tubular body 201. The size number and location of the accessory channels 214 can vary widely and are created by the geometry and number of tubes 212 present within the tubular body 201. The placement of the tubes 212 adjacent and in fluid intimate contact with the internal lumen of the main tubular body 201 at a distance from the functional orifice 204 to match with the position of the vacuum release orifice 209 creates, in addition to the on-demand valving mechanism 216, a integral debris trap for large items evacuated from the surgical field that would not be desired to be lost to the overall downstream vacuum system and contaminated vacuum trap.

Figure 3C:
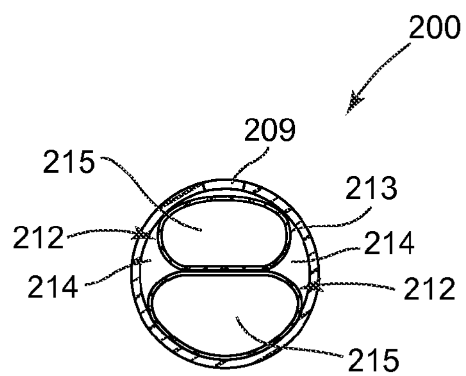
FIG. 3C is a cross-sectional view of the suction tip apparatus of FIG. 3A when the suction tip is occluded.

If any occlusion of the functional orifice 204A occurs, the pressure within the body 201 of the suction tip 200 decreases to an occlusion pressure, which is lower than the normal operating pressure. This lower pressure condition causes a second one of the tubes 212 to collapse and move inwardly away from the internal wall 205A of the tubular body 201. This inward movement causes the first tube sealing the vacuum release orifice 209 (which in some embodiments may be the same as the second tube) to uncover and unseal the vacuum release orifice 209 (FIG. 3C). When the vacuum release orifice 209 is unsealed, the peripheral channels 214 allow vacuum release and subsequent continuity of flow through the tubular body 201, ensuring iatrogenic tissue damage is minimized.

In the embodiment shown in FIGS. 3 and 4, at least one of the tubes 212 is compressed upon insertion into the tubular body 201, thus creating at least one oval shaped smooth bore tube. When the tip 200 is placed under an occlusion pressure, two accessory channels passages 214 and two main vacuum passages 215 are formed within the passage 211 of the tubular body 201.

Figure 5A:
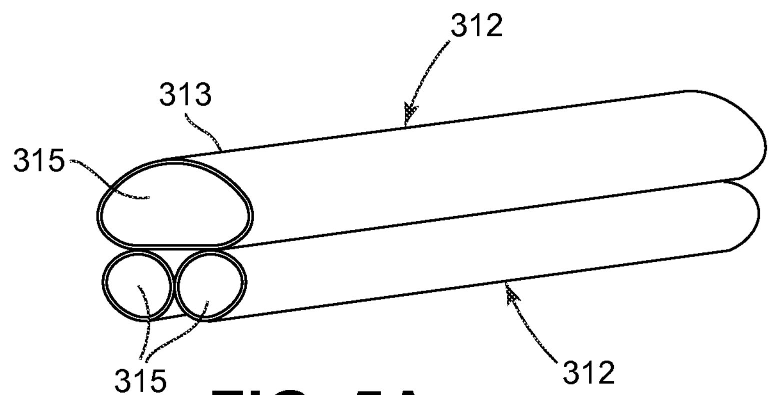
FIG. 5A is a schematic plan view of another embodiment of a tubular insert suitable for use of the suction tip apparatus of FIG. 3A.
Figure 5B:
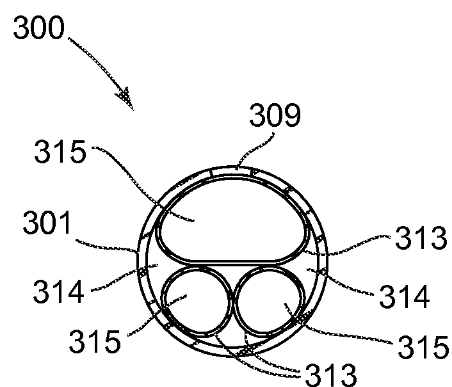
FIG. 5B is a cross-sectional view of another embodiment of the suction tip apparatus of FIG. 3A, including the tubular insert of FIG. 5A.
Figure 5C:
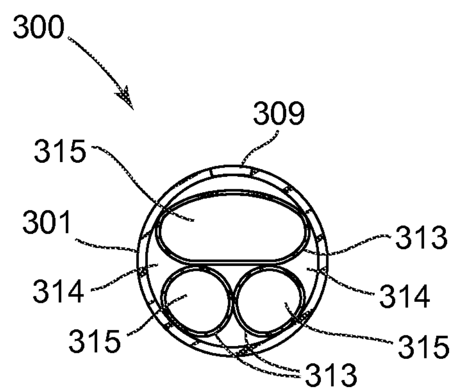
FIG. 5C is a cross-sectional view of the suction tip apparatus of FIG. 5A when the suction tip is occluded.

Referring to FIGS. 5A-5C, in an alternative embodiment of the suction tip 300, three tubes 312 with peripheral side walls 313 can be placed in the tubular body 301. At least one of the tubes 312 includes a flexible, resilient and collapsible side wall 313. The tubes 312 are oriented within the tubular body 301 such that one sealing tube occludes and seal the vacuum release orifice 309 and thus acts as a resilient valving mechanism. As shown in FIG. 5B, the tubes 312 form an plurality of accessory channels 314 within the tubular body 301. As shown in FIG. 5C, when the tubular body 301 is placed under an occlusion pressure, the side wall of a second tube 312 collapses inwardly and away from the interior wall 305A of the tubular body 301 and forms an accessory passage. This inward movement of the side wall of the second tube 312 causes a side wall of the first tube sealing the vacuum release orifice to move inwardly and disengage from the side wall 305A and unseal the vacuum release orifice 309. The combination of number of compressible tubes 312 and the properties of the engineered plastic materials selected for the tubes 312 can be selected to provide the degree of resiliency desired to control the on-demand automatic valving that controls the sealing and unsealing operation of the vacuum release orifice 309, as well as providing a means to optimize and control flow characteristics.

Figure 6A:
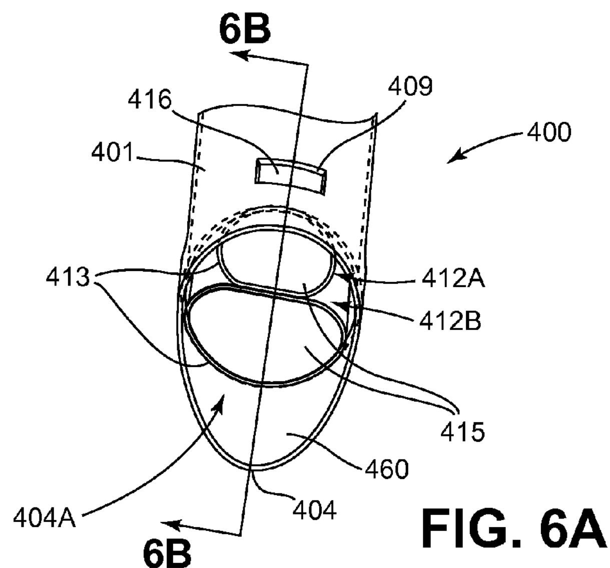
FIG. 6A is an overhead plan view of an embodiment of a suction tip apparatus having recessed tubular inserts that create an integral trap for materials dislodged in a suctioning process.
Figure 6B:
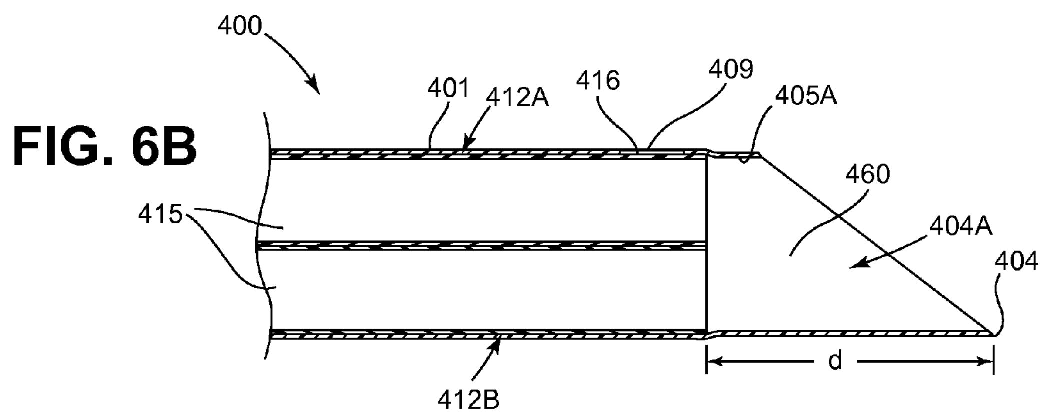
FIG. 6B is a cross-sectional view through the suction tip apparatus of FIG. 6A.
Figure 6C:
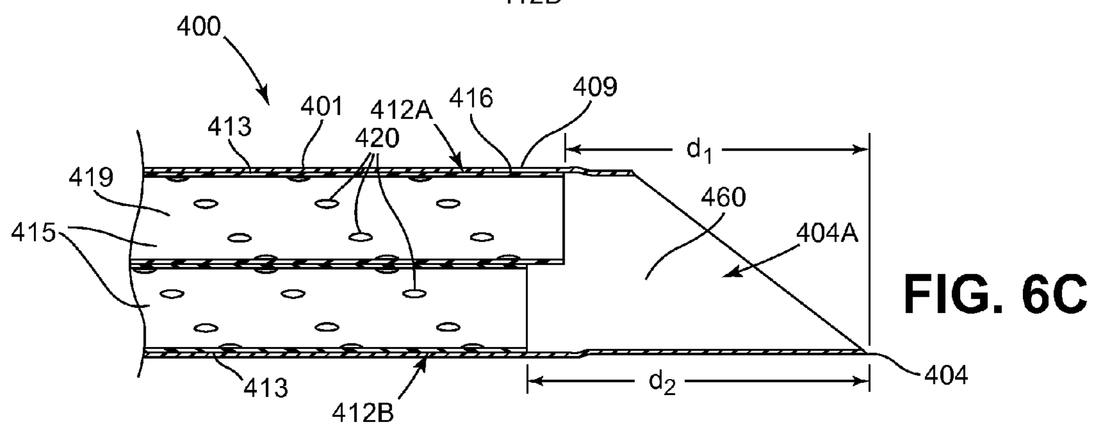
FIG. 6C is a cross-sectional view of an embodiment of a suction tip apparatus with staggered recessed tubular inserts, said inserts having a surface treatment.

Referring to FIGS. 6A-6C, in another embodiment of the suction tip 400, two compressible tubes 412A, 412B can be placed in the tubular body 401. The tubes 412A, 412B are oriented within the tubular body 401 to occlude the vacuum release orifice 409 and thus act as a resilient valving mechanism. As shown in FIG. 6B, the tubes 412A, 412B are recessed a distance d with respect to the functional tip 404, which creates a reservoir 460 within the tip 404 to collect debris dislodged during suctioning procedures. As shown in FIG. 6C, the position of the ends of the tubes 412A and 412B with respect to the functional tip 404 can be staggered and oriented at differing distances $d_1$, $d_2$, respectively, with respect to the functional tip 404 to further tailor the shape of the reservoir 460, or to adjust the flow or reduce turbulence to control the noise attenuating characteristics of the tubular body 401. When the tubular body 401 is placed under an occlusion pressure, at least one of the tubes 412A, 412B collapses inwardly and away from the interior wall 405A of the tubular body 401 and forms an accessory passage that uncovers and opens the vacuum release orifice 409.

In the embodiment shown in FIG. 6C, the exterior surface 413 and the interior surface 419 of the tubes 412A and 412B also include structures 420 to adjust and/or tailor the flow or reduce turbulence to control the noise attenuating characteristics of the tubular body 401. Any interior surface in contract with the flow of materials through the tubular body 401, such as, for example, the interior surface 405A, could also include structures to modify the flow characteristics through the tubular body 401. The structures 420 could include any type of nano-scale or micro-scale surface treatments or patterns of surface structures to optimize flow characteristics to create laminar flow and minimize turbulence in an attempt to maximally attenuate noise.

Various embodiments of the invention have been described. These and other embodiments are within the scope of the following claims.

The invention claimed is:

1. A high volume suction tip, comprising:

a tubular body with peripheral side wall, a functional orifice, and a vacuum source end;

a vacuum release orifice comprising an aperture in a wall of the tubular body, wherein the aperture is between the functional orifice and the vacuum source end;

a plurality of tubes within a lumen of the tubular body, wherein the tubes form a physical barrier to prevent evacuation of a suctioned material larger than a diameter of the tubes, have a longitudinal axis substantially parallel to a longitudinal axis of the tubular body, and provide channels within and around the tubes for transmitting the suctioned material from the functional orifice to the vacuum source end, and wherein the tubes further comprise a surface treatment selected from at least one of micro-scale and nano-scale structures, and wherein:

if the functional orifice is open, an exterior wall of a first tube engages an interior wall of the tubular body and seals the vacuum release orifice, and if the functional orifice is at least partially occluded, a compressible side wall of a second tube collapses inwardly to disengage the exterior wall of the first tube from the interior wall of the tubular body and open the vacuum release orifice, to maintain vacuum flow toward the vacuum source end of the tubular body through an accessory channel between the exterior wall of the first tube and the internal surface of the tubular body.

2. The suction tip of claim 1, wherein an accessory channel resides between an exterior wall of the tubes and the internal wall of the tubular body, and wherein, if the functional orifice is at least partially occluded, the accessory channels allow passage of materials between the exterior wall of the tubes and the internal surface of the tubular body.

3. The suction tip of claim 1, wherein the tubes are compressible, and wherein the tubes are frictionally retained within the lumen of the tubular body of the suction tip.

4. The suction tip of claim 1, wherein the tubes are bonded to the tubular body.

5. The suction tip of claim 1, wherein the lumen of the tubular body comprises at least three tubes.

6. The suction tip of claim 1, wherein the ends of the tubes proximal the functional orifice are staggered with respect to the functional orifice.

7. The suction tip of claim 1, wherein the tubes comprise a material selected from the group consisting of polymers, composites and combinations thereof.

8. The suction tip of claim 1, wherein the tubes are disposable.

9. The suction tip of claim 1, wherein the first tube and the second tube are the same tube.

10. A system comprising:

a vacuum source;

a suction conduit attached to the vacuum source, and a suction tip on the suction conduit, wherein the suction tip comprises:

a tubular body with peripheral side wall, a vacuum source end attached to the suction conduit, and a functional orifice distal the vacuum source end;

a vacuum release orifice comprising an aperture in a wall of the tubular body between the functional orifice and the vacuum source end; and a plurality of tubes retained within a lumen of the tubular body, wherein the tubes form a debris trap to prevent evacuation of a suctioned material larger than a diameter of the tubes, and have a longitudinal axis substantially parallel to a longitudinal axis of the tubular body and provide within and around the tubes at least one channel for transmitting a suctioned material from the functional orifice of the tubular body to the vacuum source end, and wherein the tubes further comprise a surface treatment selected from at least one of micro-scale and nano-scale structures, and wherein:

if the functional orifice is open, an exterior wall of a first tube engages an interior wall of the tubular body and closes the vacuum release orifice, and if the functional orifice is at least partially blocked, a compressible side wall of a second tube collapses away from the interior wall of the tubular body to disengage the exterior wall of the first tube from the vacuum release orifice and wherein vacuum flow is maintained toward the vacuum source end of the tubular body through an accessory channel between the exterior wall of the first tube and the internal surface of the tubular body.

11. The system of claim 10, wherein the accessory channel has a longitudinal axis substantially parallel to the longitudinal axis of the compressible tube.

12. The system of claim 11, wherein the dimensions of the accessory channel vary based on the operating pressure of the system.

13. The system of claim 11, wherein the accessory channel is between the exterior surface of the compressible tube and the vacuum release orifice, such that the vacuum release orifice is an open aperture.

14. The system of claim 10, further comprising a vacuum on-off valve between the suction tip and the vacuum source.

15. The system of claim 10, wherein the vacuum source further comprises a vacuum trap.

16. The system of claim 10, wherein the tubes are staggered within the lumen of the tubular body.

17. The system of claim 10, wherein the suction tip comprises three or more tubes.

18. A kit comprising a suction conduit;

a suction tip comprising a tubular body with peripheral side wall, a vacuum source end suitable for attachment to the suction conduit, and a functional orifice distal the vacuum source end, and a vacuum release orifice comprising an aperture in a wall of the tubular body between the functional orifice and the vacuum source end; and at least one compressible tube suitable for insertion into a lumen of the tubular body, wherein the tubes form a debris trap to prevent evacuation of a suctioned material larger than a diameter of the tubes, wherein the tubes further comprise a surface treatment selected from at least one of micro-scale and nano-scale structures, and wherein, when retained within the lumen, an exterior surface of a side wall of the at least one compressible tube closes the vacuum release orifice.

19. The kit of claim 18, wherein the tubes are disposable.

* * * * *